United States Patent
Simopoulos et al.

(10) Patent No.: US 6,398,733 B1
(45) Date of Patent: Jun. 4, 2002

(54) MEDICAL ULTRASONIC IMAGING SYSTEM WITH ADAPTIVE MULTI-DIMENSIONAL BACK-END MAPPING

(75) Inventors: Constantine Simopoulos, Menlo Park; Kutay F. Ustuner, Mountain View; Anming He Cai, San Jose; John Jackson, Menlo Park, all of CA (US); Matthew O'Donnell, Ann Arbor, MI (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/556,354

(22) Filed: Apr. 24, 2000

(51) Int. Cl.⁷ .................................................. A61B 8/00
(52) U.S. Cl. ...................................... 600/443; 73/631
(58) Field of Search .................................. 600/437, 440, 600/443, 447; 382/128–130; 73/631

(56) References Cited

U.S. PATENT DOCUMENTS

| | | | |
|---|---|---|---|
| 4,852,576 A | | 8/1989 | Inbar et al. |
| 4,907,156 A | * | 3/1990 | Doi et al. ...................... 382/19 |
| 5,289,374 A | * | 2/1994 | Doi et al. .................... 600/407 |
| 5,313,948 A | * | 5/1994 | Murashita et al. .......... 600/443 |
| 5,579,768 A | | 12/1996 | Klesenski |
| 5,670,719 A | * | 9/1997 | Madsen et al. ................ 73/619 |
| 5,827,942 A | * | 10/1998 | Madsen et al. ............... 73/1.82 |
| 5,841,889 A | * | 11/1998 | Seyed-Bolorforosh ...... 600/443 |
| 5,954,653 A | | 9/1999 | Hatfield et al. |
| 5,993,392 A | | 11/1999 | Roundhill et al. |
| 6,102,859 A | * | 8/2000 | Mo ............................. 600/443 |
| 6,120,446 A | * | 9/2000 | Ji et al. ....................... 600/437 |
| 6,176,828 B1 | * | 1/2001 | Beches et al. ............... 600/440 |

FOREIGN PATENT DOCUMENTS

EP          0 843 181 A1       5/1998

* cited by examiner

Primary Examiner—Francis J. Jaworski
(74) Attorney, Agent, or Firm—Brinks Hofer Gilson & Lione

(57) ABSTRACT

A medical ultrasonic imaging system uses an adaptive multi-dimensional back-end mapping stage to eliminate loss of information in the back-end, minimize any back-end quantization noise, reduce or eliminate electronic noise, and map the local average of soft tissue to a target display value throughout the image. The system uses spatial variance to identify regions of the image corresponding substantially to soft tissue and a noise frame acquired with the transmitters turned off to determine the mean system noise level. The system then uses the mean noise level and the identified regions of soft tissue to both locally and adaptively set various back-end mapping stages, including the gain and dynamic range.

56 Claims, 10 Drawing Sheets

$$\left.\frac{dD}{dI_n}(\underline{x})\right| = \text{FIXED}$$
$$I_n(\underline{x}) = \overline{I}_t(\underline{x})$$

MEDICAL ULTRASONIC IMAGING SYSTEM WITH ADAPTIVE MULTI-DIMENSIONAL BACK-END MAPPING

BACKGROUND

The present invention relates to medical ultrasonic imaging, and in particular to systems that adaptively set one or more stages of back-end mapping that may include gain, dynamic range and post-processing map stages in one or more image dimensions to improve such imaging.

In conventional ultrasonic imaging, a B-mode signal is adjusted for gain and dynamic range before it is mapped to a range of gray levels or colors for display. The dynamic range of the signal to be displayed can conventionally be set by the user by means of a display dynamic range control. This control is conventionally independent of range and azimuthal position in the image. The gain can conventionally be varied by the user using a depth gain compensation (DGC) or a time gain compensation (TGC) control along with the master gain or B gain control. The DGC and TGC controls are conventionally variable in range (axial dimension) only, and the master gain is independent of both range and lateral (azimuthal) position. A few systems also offer lateral gain compensation in addition to depth gain compensation, but the two one-dimensional gain controls comprise only an approximation to a true two-dimensional gain control.

After gain and display dynamic range have been applied, log-compressed B-mode signals are re-quantized, typically to 8-bit or 256 quantization levels. The quantization step (in dB) is given by the ratio of the dynamic range selected by the user to the number of quantization levels.

After quantization, a post-processing map is used to map the quantization levels to a range of gray levels or colors. This map can be a selected one of a predesigned set of maps or alternately a user-designed map. These maps are also conventionally range and azimuth independent.

On commercially available ultrasound imaging systems, gain controls are often used by the users to adjust the brightness level. In many cases, users adjust the gain mainly to keep the regional mean of the soft tissue gray level within a narrow range of gray values across the image. This preferred range is consistent from user to user, and in many cases users tend to adjust the gain to set the gray level for soft tissue roughly to the 64th gray level on a linear map that maps 0 to black and 255 to white. However, gain adjustments for soft tissue brightness level and uniformity do not simultaneously optimize noise suppression and prevent display saturation. For this reason, gain and/or dynamic range are frequently sub-optimal for some or all parts of an image. As a result, information can be lost by cutting off low-level signals or saturating high-level signals.

Such loss of information due to errors in setting gain and/or dynamic range can be reduced or eliminated by setting the dynamic range to a very high level. This approach however reduces contrast resolution because different tissue types are then mapped to similar gray levels, thereby reducing the prominence of echogenicity differences.

U.S. Pat. No. 5,579,768 to Klesenski (assigned to the assignee of the present invention) proposes an automatic gain compensation system that uses B-mode intensity of image signals to identify regions of soft tissue, and then automatically sets these regions of soft tissue to a predetermined magnitude.

U.S. Pat. No. 5,993,392 to Roundhill discloses an ultrasonic imaging system in which dynamic range is selected based upon the range and azimuthal position of the image signal within the frame. The disclosed system is not responsive to the image signal itself, and therefore cannot be considered to be an adaptive system. Rather, the approach used in the Roundhill patent is to select a stored compression map as a function of the range and azimuth of the display signal.

SUMMARY

Conventional ultrasound imaging systems use various control stages in the backend to map a range (window) of input signal levels to a range of display gray levels or colors. These stages may include a single or multiple gain stages, a dynamic range control stage, post processing maps, etc. The dynamic range control allows users to adjust the width of the window of input signal levels to be displayed. We will refer to this user control as the display dynamic range control to differentiate it from other possible windowing operations a system might have. The gain controls let the user adjust the position of this window. Therefore, the dynamic range and gain stages together determine the actual window of input signal levels to be displayed without saturation. A post-processing map then determines the actual gray levels and or colors that correspond to the signal levels thus selected for display.

Ideally, the display dynamic range should be set equal to the dynamic range of the input signal, and the gain should be set to match the full range of input signal to the full range of displayed values. In this way, no signal is lost and the back-end quantization noise is minimized. In addition, the regional mean of the soft tissue signal should be mapped to a particular display level (e.g., gray level) uniformly across the image for display uniformity.

The dynamic range of a B-mode signal is determined by the noise level of the system and the maximum echo level. The noise level of the system is range and azimuth dependent, due to range and azimuth dependent front-end gain and imager aperture size. The maximum echo level is determined by the transmit field strength, the attenuation of the medium, the reflectivity of the object being observed, and the coherent gain of the receive beamformer. For these reasons, an adaptive and multi-dimensional back-end mapping stage or stages are required to achieve the above-mentioned mapping goals.

We here describe an adaptive and multi-dimensional method that a) prevents loss of information in the back-end, b) reduces or eliminates electronic noise in the displayed images, c) minimizes the back-end quantization noise and d) for B-mode, maps the regional mean of soft tissue to a programmable target display level for tissue. We also describe several reduced implementations that satisfy a subset of the above list. The reduced implementations adaptively adjust gain and in some cases dynamic range in two dimensions to display images substantially free of electronic noise and to display tissue at a target tissue gray level.

Note that the term "input signal" is used broadly to refer to amplitude, intensity or log-compressed amplitude of the beamformer output (i.e. B-mode signal) as well as to any parameter of interest derived or extracted from the beamformer output, including the average velocity and power estimates of the Doppler frequency shift (i.e. Color Doppler Mode signals) and the power spectrum estimate of the Doppler frequency shift (i.e., Spectral Doppler Mode signals). The foregoing paragraphs have been provided by way of introduction, and they are not intended to limit the scope of the following claims.

DETAILED DESCRIPTION OF THE PRESENTLY PREFERRED EMBODIMENTS

Figure 1:
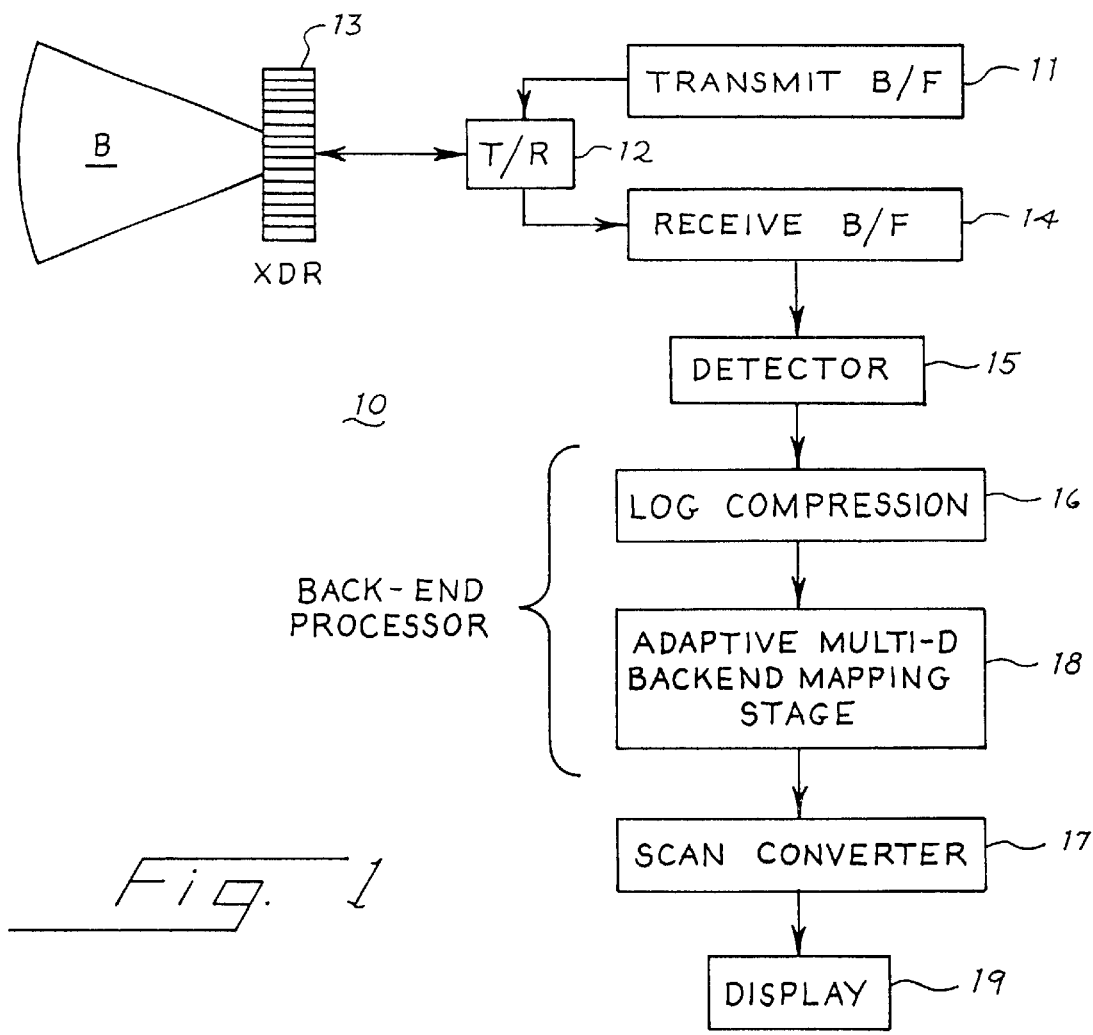
FIG. 1 is a block diagram of a medical diagnostic ultrasonic imaging system that incorporates a preferred embodiment of this invention.

Turning now to the drawings, FIG. 1 is a block diagram of a medical diagnostic ultrasonic imaging system 10 that incorporates a preferred embodiment of this invention. As shown in FIG. 1, a transmit beamformer 11 applies transmit waveforms via a transmit/receive switch 12 to a transducer array 13. The transducer array 13 produces ultrasonic pulses in response to the transmit waveforms, which pulses are directed into a body B to be imaged. Returning echoes from the body B impinge upon the transducer array 13, which converts these echoes into receive signals that are transmitted via the transmit/switch 12 to a receive beamformer 14. The receive beamformer 14 applies appropriate delays and phase shifts to cause the receive signals from selected locations within the body B to add coherently. These beamformed signals are applied to an amplitude detector 15 and a back-end processor that includes a log compression device 16 before being applied to a scan converter 17. The scan converter 17 generates display values upon a grid appropriate for a display 19.

All of the elements 11–17 and 19 can take any suitable form, and are not limited to any particular implementation. For example, the transmit and receive beamformers can be constructed as analog or digital devices, and any suitable transducer array can be used, including a single-element transducer array and phased arrays of various dimensions. Also, the system 10 may include additional elements in the signal path between the transducer array 13 and the display 19, and selected ones of the illustrated elements may be deleted or the order of some of the elements may be switched. For example the order of the back-end processor and scan converter 17 can be altered.

The back-end processor also includes an adaptive multidimensional back-end mapping stage 18 that incorporates a preferred embodiment of this invention. This mapping stage 18 can take many forms, and four specific embodiments are described below.

First Preferred Embodiment

Figure 2:
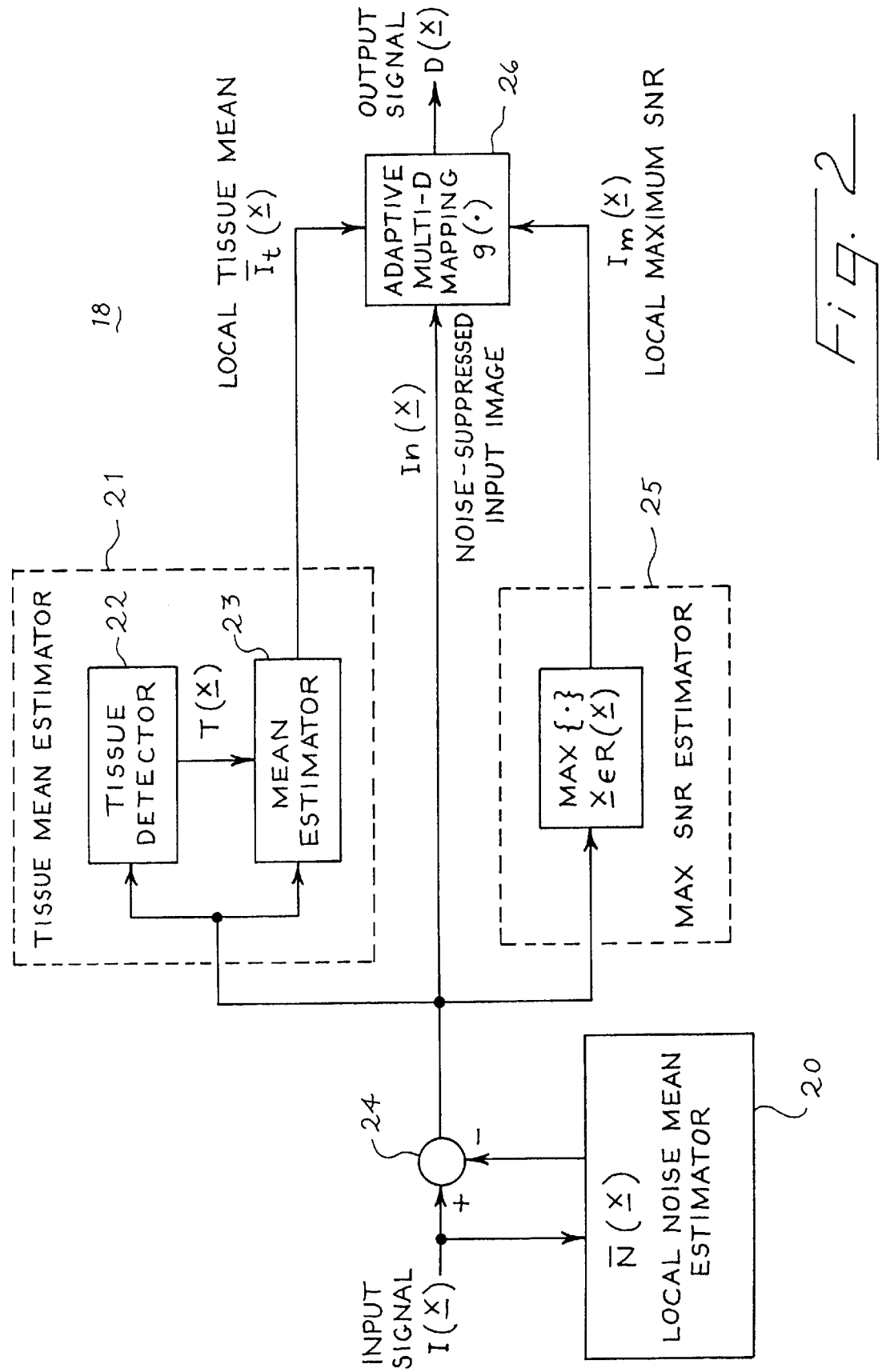
FIG. 2 is a block diagram of a first preferred embodiment of the multi-dimensional back-end mapping stage of FIG. 1.

FIG. 2 shows a block diagram of a general embodiment of the mapping stage 18. The embodiment of FIG. 2 receives an input signal I(x) generated by the log compression device 16. Simply by way of example, the input signal can be a B-mode image signal.

The input signal I(x) and a local noise mean estimate generated by an estimator 20 are applied to a summer 24. The local noise mean estimator 20 estimates the local noise of the system as a function of position within an image. As explained in greater detail below, several approaches can be used to estimate the local noise mean. For example, one or more frames of image data may be acquired without applying transmit signals to the transducer elements of the transducer 13. In the absence of an insonifying pressure wave, the resulting input signal forms a noise frame that is a measure of currently-prevailing system noise as a function of position within the image. This noise frame can then be filtered with a low pass filter in the estimator 20 in order to generate the local noise mean $\overline{N}(x)$. This parameter is subtracted from the input signal I(x) in the summer 24. The output of the summer 24 represents a noise suppressed input signal $I_n(x)$, which is applied in parallel to a tissue mean estimator 21, a maximum SNR estimator 25 and an adaptive multi-dimensional mapping stage 26.

The tissue mean estimator 21 processes the noise suppressed input signal $I_n(x)$ to develop an output signal $\overline{I}t(x)$ that is indicative of the local mean of $I_n(x)$ for those portions of $I_n(x)$ acquired from soft tissue.

The tissue mean estimator 21 includes a tissue detector 22 and a mean estimator 23. The tissue detector identifies those portions of $I_n(x)$ characteristic of soft tissue and generates an output signal T(x) which is in the logic state 1 for values of x associated with soft tissue and is in the logic state 0 for values of x not associated with soft tissue. The tissue detector 22 can take many forms, and it can operate by comparing the variance of $I_n(x)$ with a target value characteristic of soft tissue, as described in greater detail below. Alternatively, the tissue detector 22 can use amplitude techniques to detect soft tissue, as described in Klesenski U.S. Pat. No. 5,579,768. The tissue detector 22 implements Eq. 1:

$$R(X_0) = \{T(x)=1\} \cap \{|X-X_0| \leq W_t\} \quad \text{(Eq. 1)}$$

In Eq. 1 $W_t$ is the width array that defines the region R around $x_o$.

The mean estimator 22 uses $I_n(x)$ and T(x) to implement Eq. 2:

$$\overline{I}_t(X_0) = [I_n(X)]_{x \in R(x_0)} \quad \text{(Eq. 2)}$$

In Eq. 2 the symbol [·] is the mean operator over x within the region R which is a function of the position $x_0$.

If $R(x_0)$, is empty for a given $W_t$ (i.e. there is no soft tissue within the distance $W_t$ around $x_0$), then we either increase $W_t$ until R is not empty or interpolate/extrapolate $\overline{I}_t(x)$ around $x_0$ to determine $\overline{I}_t(x_0)$. Note that $W_t$ can be dependent upon ($x_0$) or not. For example $W_t(x_0)$ can be set as a function of the lateral and axial resolution at ($x_0$).

In an alternative embodiment, T(x) can be a tissue map which indicates the likelihood that the image at position x was acquired from soft tissue, wherein the map assumes intermediate values between 0 and 1, and increasing values for the tissue map correspond to increasing levels of likelihood that the associated input signal was acquired from soft tissue. In this case, T(x) can be used as a weight in computing $\bar{I}_t(x)$. In addition T(x) can also be superimposed on a B-Mode image to enhance tissue differences.

The maximum SNR estimator 25 implements Eq. 3:

$$I_m(x_0) = \max_{|x-x_0| \leq W_m} \{I_n(x)\} \quad \text{(Eq. 3)}$$

In Eq. 3, the function MAX{·} is the maximum operator; $W_m$ is the width array that defines the region R around $x_0$. If desired, $W_m$ can be set equal to $W_t$ described above. The maximum SNR estimator 25 can operate on point SNR values (equal to $I_n(x)$ in this example), or alternately the estimator 25 can operate with an average SNR over a portion of the image signal. The region over which the estimator 25 operates can be a portion of a current image frame, an entire current image frame, a previous image frame, or two or more image frames. The estimator 25 generates an output signal $I_m(x)$ which defines the local maximum SNR in the selected portion of the input signal.

The adaptive multi-dimensional mapping stage 26 responds to the input signals $I_n(x)$, $\bar{I}_t(x)$, and $I_m(x)$ to generate an output signal D(x) for display. In the embodiment of FIG. 2, the stage 26 is shown as a single stage that can be implemented as a single look-up table. Alternatively, the various functions performed by the mapping stage 26 can be implemented by a variety of mapping devices including adders, multipliers and look-up tables, which can be placed together or separately at various stages in the signal path between the receive beamformer 14 and the display 19.

In the example of FIG. 2, the mapping stage 26 implements the following equation:

$$D(x) = g(I(x), \bar{N}(x), \bar{I}_t(x), I_m(x), D_t D_m, \ldots) \quad \text{(Eq. 4)}$$

Figure 4:
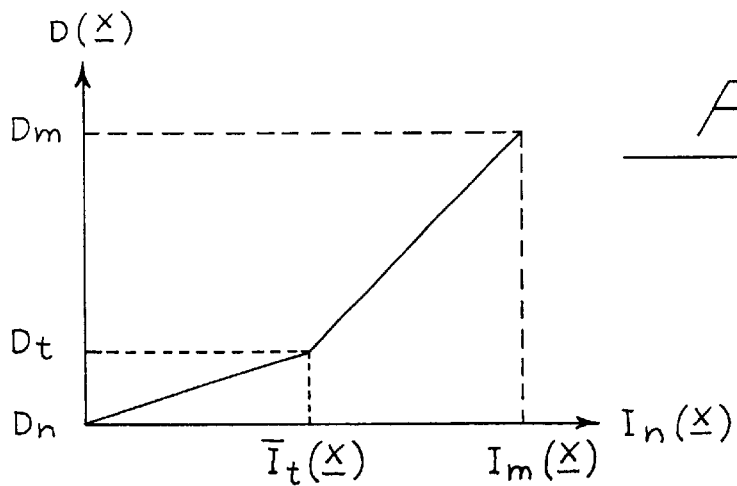
FIGS. 4, 5, and 6 are graphs used to illustrate alternative mapping functions performed by the embodiment of FIG. 2.

The function g implemented by the mapping stage 26 can be the function identified in Eq. 5 and illustrated in FIG. 4.

$$D(x) = \begin{cases} D_n = 0 & I_n(x) \leq 0 \\ \dfrac{D_t}{\bar{I}_t(x)} I_n(x) & 0 < I_n(x) \leq \bar{I}_t(x) \\ \dfrac{D_m - D_t}{I_m(x) - \bar{I}_t(x)}(I_n(x) - \bar{I}_t(x)) & \bar{I}_t(x) < I_n(x) \leq I_m(x) \\ D_m & I_n(x) > I_m(x) \end{cases} \quad \text{(Eq. 5)}$$

where $I_n(x) = I(x) - \bar{N}(x)$.

Note that values of $I_n(x)$ equal to 0 are mapped to the noise target display value $D_n$, which equals 0 in this example. Values of the signal $I_n(x)$ equal to the local tissue mean $\bar{I}_t(x)$ are mapped to the soft tissue target display value $D_t$, and values of the signal $I_n(x)$ equal to the local maximum SNR $I_m(x)$ are set equal to the maximum target display value $D_m$.

Figure 5:
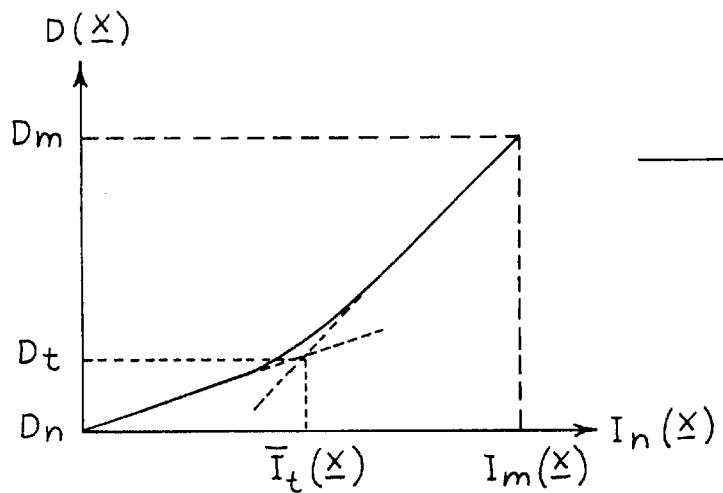

The mapping function g of Equation 4 can of course be varied from the foregoing example. For example, as shown in FIG. 5 a polynomial spline function may be used to eliminate the discontinuity in the slope of the map around $I_n(x) = \bar{I}_t(x)$ This results in a less precise mapping of $I_n(x)$ to $D_t$ when $I_n(x)$ is equal to the local soft tissue mean.

Figure 6:
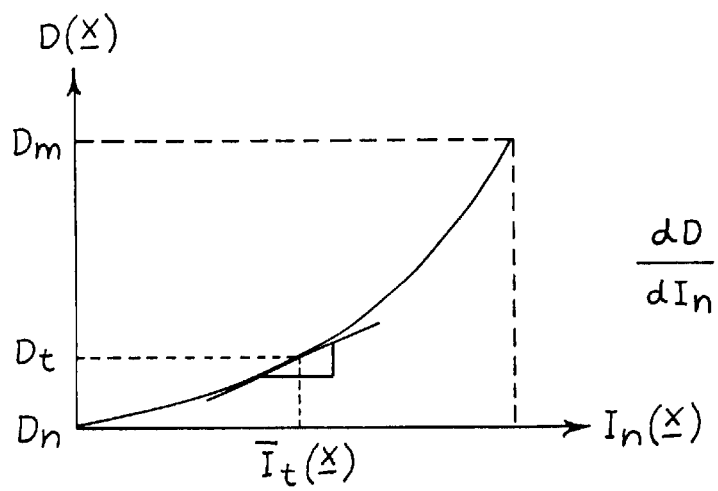

FIG. 6 shows another approach that controls the slope of the curve around values of $I_n(x) = \bar{I}_t(X)$.

Figure 3:
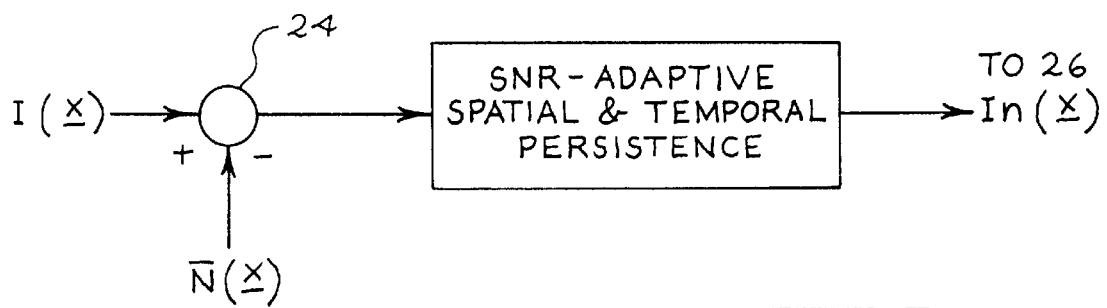
FIG. 3 is a block diagram of a modification to the embodiment of FIG. 2.

Other alternatives are possible. For example, as shown in FIG. 3 an SNR-adaptive spatial and temporal persistence filter can be interposed between the summer 24 and the mapping stage 26. This filter can be used to reduce noise for input values with low SNR, without giving up temporal or spatial resolution for input signals with sufficient SNR.

Figure 7:
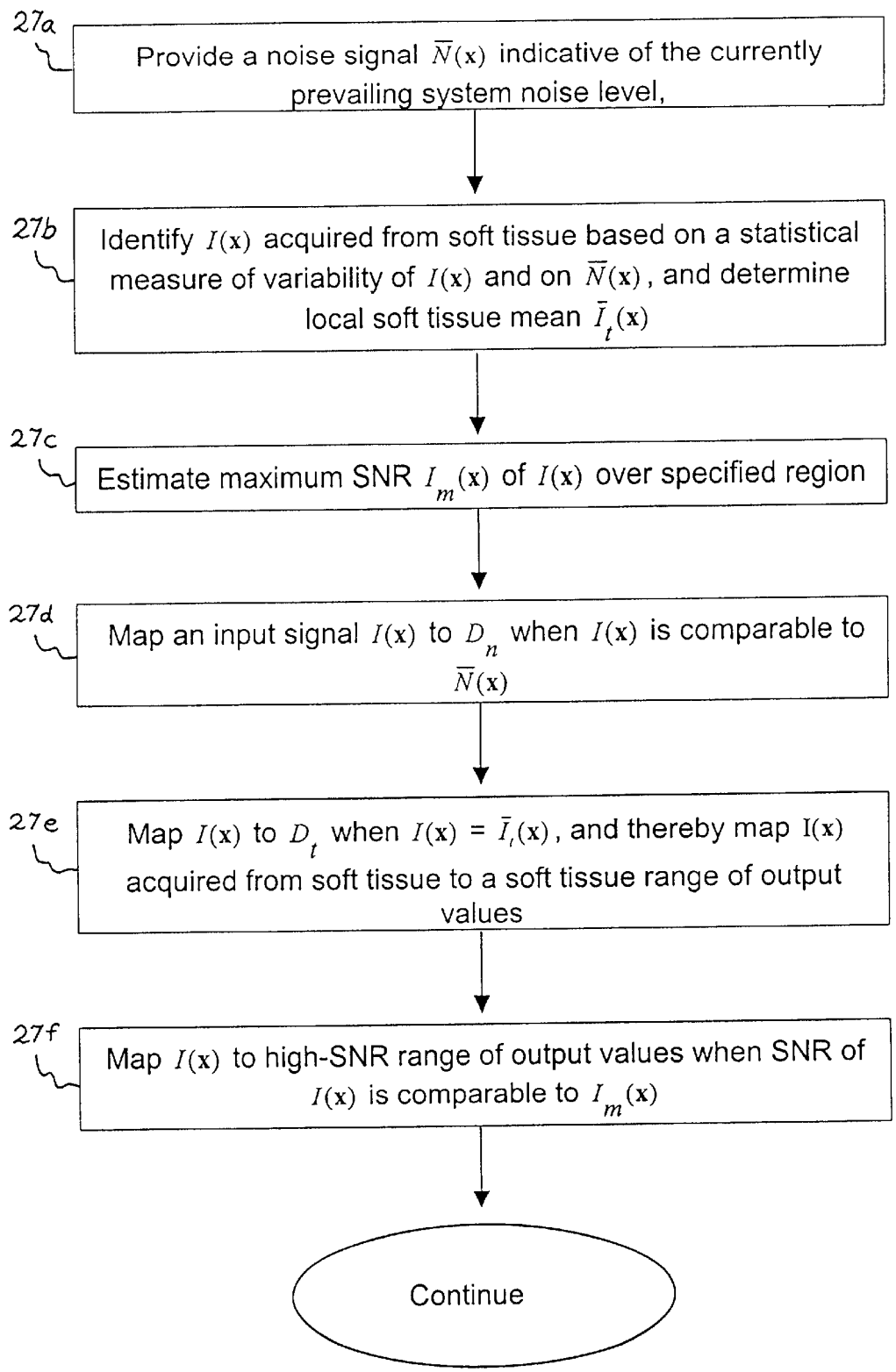
FIG. 7 is a flow chart of a method performed by the embodiment of FIG. 2.

FIG. 7 provides a flow chart of a method implemented by the embodiment of FIG. 2. In block 27a, a local mean noise signal $\bar{N}(x)$ is provided that is indicative of the currently prevailing system noise level. This can be done using noise frames as described above. Alternatively, a computer model of the imaging system can be used to estimate the local noise mean as a function of the currently prevailing imaging parameters. Other approaches also can be used. The local noise mean $\bar{N}(x)$ may vary as a function of one, two or more spatial dimensions of the image. Thus, the term "providing" is intended broadly and is not limited to any single approach.

In 27b those portions of I(x) acquired from soft tissue are identified based on a statistical measure of variability of I(x) and on $\bar{N}(x)$, and these portions are then used to determine a local soft tissue mean $\bar{I}_t(x)$. As explained above, $\bar{I}_t(x)$ is representative of the mean or average amplitude of the noise-suppressed input signal for those portions of the input signal representative of soft tissue.

At 27c the maximum SNR $I_n(x)$ of I(x) is estimated over a specified region, which as explained above may vary depending upon the application.

At 27d an input signal I(x) is mapped to $D_n$ when I(x) is comparable to $\bar{N}(x)$. That is, the output signal D(x) is set equal to a selected value when I(x) is comparable to $\bar{N}(x)$. Since $\bar{N}(x)$ varies locally across an image, this provides the advantage that throughout the image values of the input signal I(x) comparable to the noise level are mapped to a range of output signal levels around $D_n$.

At 27e the noise suppressed input signal is mapped to $D_t$ when it is equal to $\bar{I}_t(x)$. In this way the input signal I(x) that is acquired from soft tissue is mapped to a soft tissue range of values of D(x) around $D_t$. Note that block 27e is specific to B-mode type input signals.

At 27f I(x) is mapped to a high SNR range of D(x) values around $D_m$ whenever the SNR of I(x) is comparable to $I_m(x)$. In addition to B-mode type input signals, block 27f is also applicable to Color Doppler Power Mode and Spectral Doppler Mode input signals.

From this explanation it should be apparent that the system of FIG. 2 adaptively maps the input signal I(x) in such a way as to present the user with an image that meets the following three criteria:

1. Throughout the image frame, input signals that are comparable to noise are mapped to a range of values around a noise target value $D_n$.
2. Throughout the image frame, B-mode type input signals associated with soft tissue are mapped to a range of values around a soft tissue target value $D_t$.
3. Throughout the image frame, input signals having an SNR comparable to the local maximum SNR are mapped to a range of values around a target display value $D_m$.

For example, $D_n$ may be at or near black, $D_m$ may be at or near white, and $D_t$ may be a specified range of gray levels, e.g., gray levels around 64 in a system where 0 corresponds to black and 255 to white.

The parameter x is used to signify a point on any one, any two, any three, or all four of the azimuth, range, elevation and time (frame number) axes or dimensions.

Of course, many variations are possible. For example, it is not required that the darkest possible display level be associated with the local mean noise level and that the brightest possible display level be associated with the local maximum SNR. If desired, a narrower range of display levels can be used. For example, the input signal can be mapped to a range of display levels smaller than the total number of available levels. Also, the mapping functions described above may be used in combination with other constraints. For example, constraints may be applied to how fast $\bar{I}_t(x)$ and or $I_m(x)$ can vary across the image or from frame to frame. Also, $D_t$ can be varied as function of SNR to address the cases where the local mean soft tissue level is too close to the local mean noise level. It is also not essential that the input signal itself be mapped to the various target levels described above. In an alternative embodiment a function of the input signal may be mapped to these levels.

Additional Embodiments

It is not essential in all embodiments that all of the functions described above in conjunction with FIG. 2 be combined. Various groupings of selected ones of these functions are also useful. For example, the embodiment described below in conjunction with FIG. 9 controls the local gain in both the near field and far field of the image such that soft tissue is displayed at a substantially constant target value. The embodiments described below in conjunction with FIGS. 14 and 15 additionally adjust the dynamic range of the displayed image locally to optimize the display in view of the currently-prevailing image signals.

Figure 8:
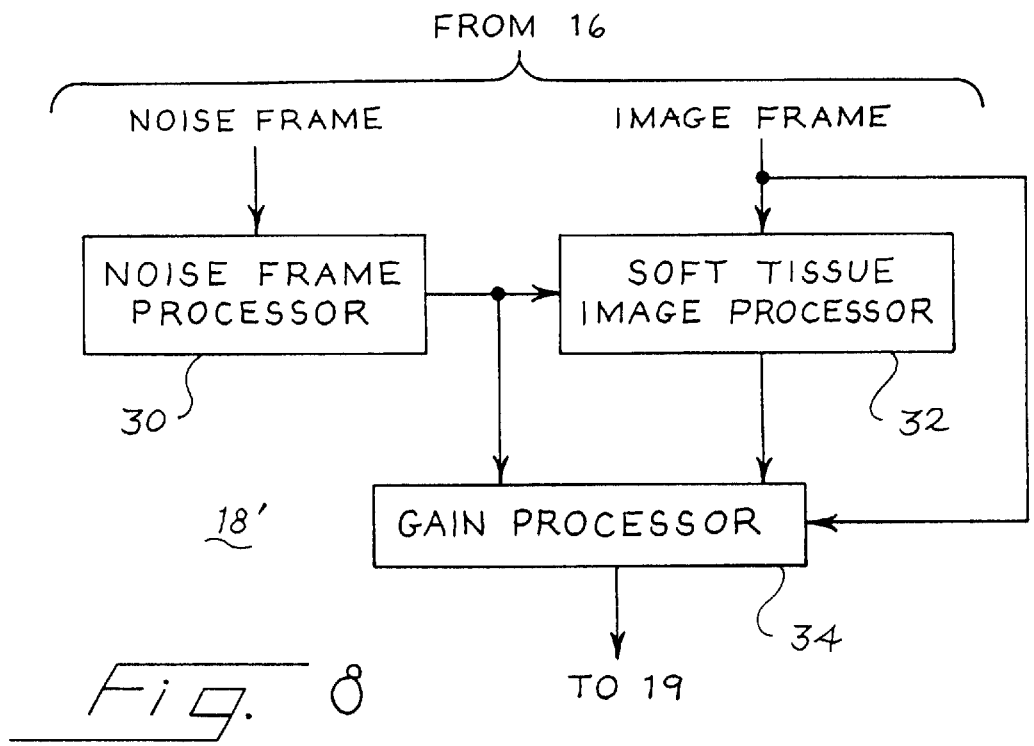
FIG. 8 is a block diagram of another embodiment of the adaptive multidimensional back-end mapping stage of FIG. 1.

FIG. 8 provides a block diagram of these embodiments of a mapping stage 18' of FIG. 1. As shown in FIG. 8, the mapping stage 18' includes a noise frame processor 30, a soft tissue processor 32, and a gain processor 34. The noise frame processor 30 generates an estimate of electronic noise as it varies over the frame. The soft tissue processor 32 generates a smoothed surface indicative of the intensity of soft tissue within an image frame at various locations in the frame. The gain processor 34 uses outputs from the processors 30 and 32 to adaptively adjust either the gain or both the gain and the dynamic range applied to the image frame.

Figure 9:
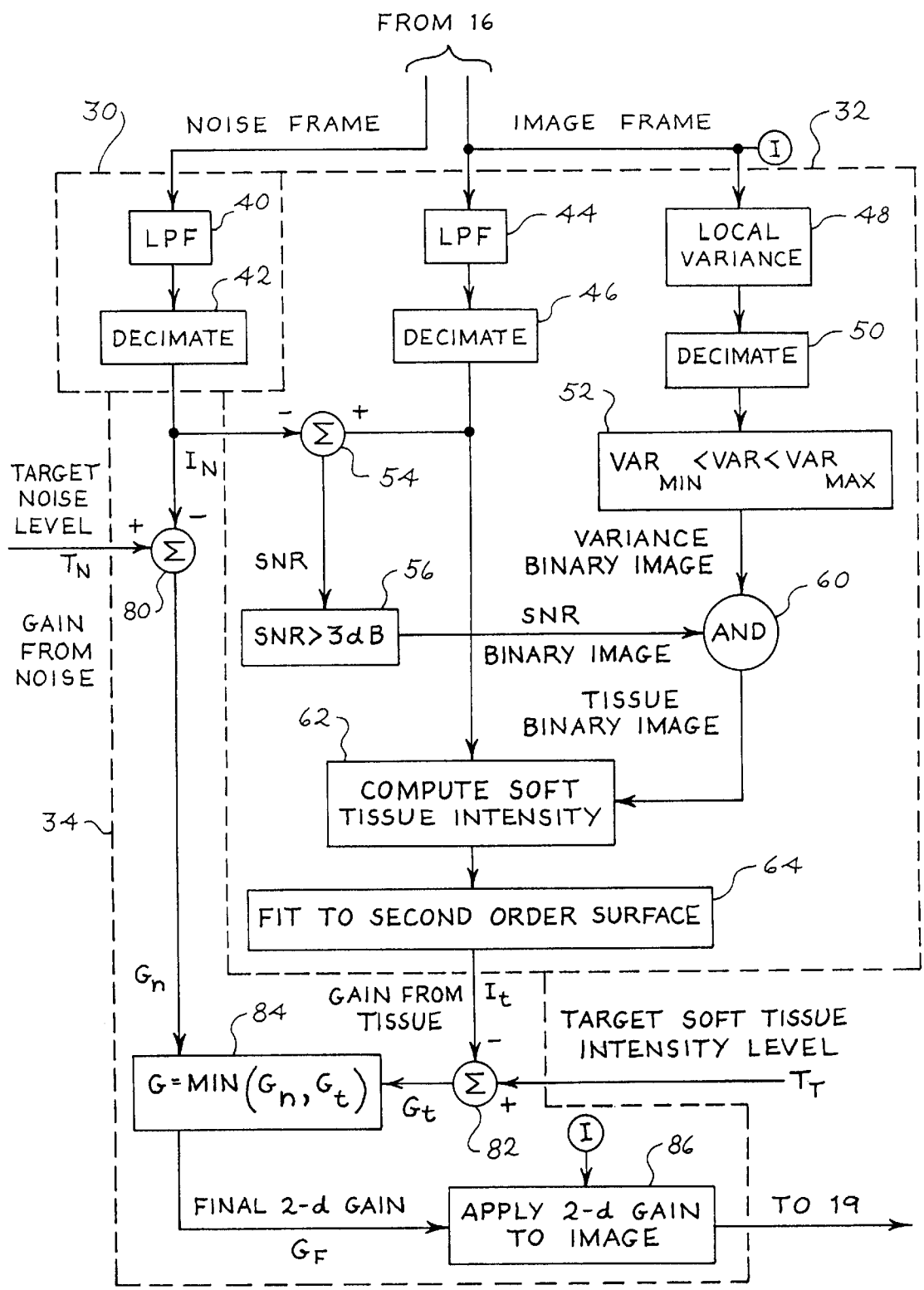
FIG. 9 is a more detailed block diagram of a first preferred embodiment of the mapping stage of FIG. 8.
Figure 10:
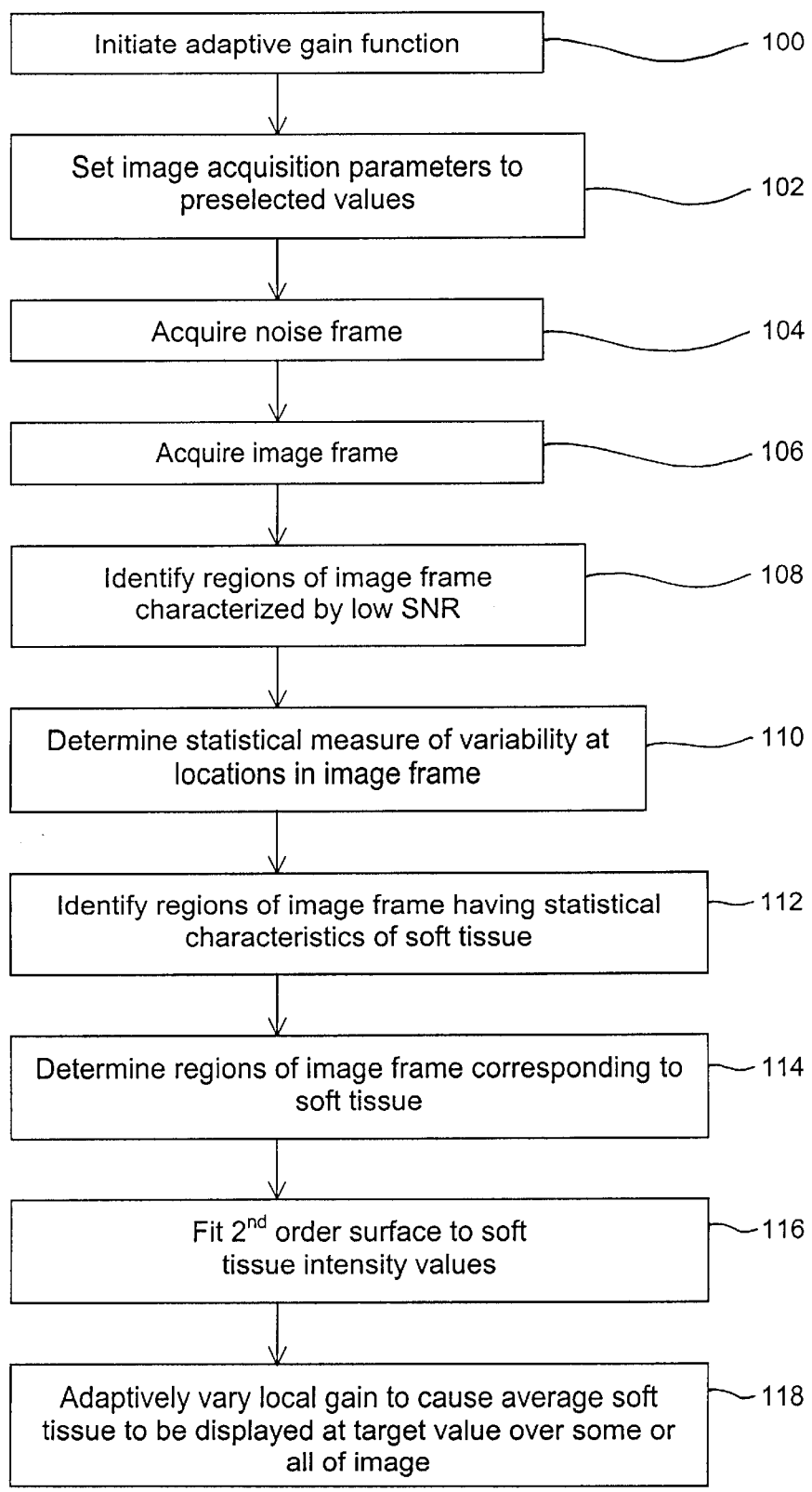
FIG. 10 is a flowchart of a method implemented by the embodiment of FIG. 9.

FIG. 9 provides a more detailed block diagram of the one preferred embodiment of the elements of FIG. 8, and FIG. 10 provides a flow chart of a method implemented by the embodiment of FIG. 9.

As shown in FIG. 9, the noise frame processor 30 in this embodiment includes a low pass filter 40 and a decimator 42, and the processor 30 generates a measure of average electronic noise at various locations distributed throughout the frame. The noise processor 30 accepts as an input a noise frame, i.e. a frame of image data acquired with the transmitters turned off. The low pass filter 40 smoothes the noise frame, and the decimator 42 decimates the filtered noise to a coarser grid, measuring for example 50 pixels on a side.

The soft tissue processor 32 responds to an image frame of data which is acquired with standardized imaging parameters as described below and which includes data from soft tissue in the image. The soft tissue processor 32 includes a low pass filter 44 and a decimator 46 that are preferably identical to the corresponding elements of the noise processor 30. The filtered, decimated noise frame from the noise processor 30 is summed with negative polarity with the filtered, decimated image frame in a summer 54. Since the noise frame and the image frame are in this example post-detection, post-compression signals, the summation performed by the summer 54 generates an output signal equal to the signal to noise ratio (SNR) for the associated region of the two frames. This SNR signal is applied to a comparator 56 that generates as an output an SNR binary image. This binary image is set equal to one in regions of the frame characterized by an SNR greater than a predetermined value, e.g., 3 dB, and to zero in regions where the SNR is less than or equal to 3 dB. Thus the SNR binary image identifies regions of the image frame that have a sufficiently high SNR to be candidates for soft tissue image signals. The portions of the SNR binary image characterized by the logic value zero correspond to high-noise, low-SNR regions of the image, and these regions are not considered candidates for soft tissue.

The soft tissue processor 32 also generates a variance binary image by means of a local variance calculator 48, a decimator 50 and a comparator 52. These elements use the local spatial variance of the image frame to identify regions of the image frame having a variance characteristic of soft tissue.

In soft tissue there are a large number of scatterers present in each resolution cell. Fully developed speckle occurs due to random interference between the reflected signals, and the amplitude of the signal obeys the Rayleigh distribution in regions of the image frame depicting soft tissue. In this embodiment, the degree to which local variance, calculated in a few resolution cells around each image pixel, resembles that of fully developed speckle is used as a measure of the likelihood that a particular image pixel represents an image of a soft tissue. The variance binary image is set equal to one in regions where the variance is consistent with soft tissue imaging and to zero otherwise.

The local variance calculator 48 operates by dividing the image into a grid of smaller regions. The size of these regions is preferably on the order of 10 times longer along each axis than the resolution size of the image.

The spatial variance $V_{i,j}$ of the center of a region or cell C having the coordinates (i, j) can be calculated as follows:

$$V_{i,j} = \frac{1}{N^2} \sum_{k,l=1}^{N} (I_{i+k,j+l} - \langle I \rangle)^2. \qquad \text{(Eq. 6)}$$

The decimator 50 preferably operates at the same scale as the decimators 42 and 46. The decimated variance frame is then compared element by element with minimum and maximum variance levels in the comparator 52. This comparison is particularly straightforward for log compressed data, where the variance of fully developed speckle characteristic of soft tissue is $(5.57 \text{ dB})^2$. Thus, regions of soft tissue in the image frame will be characterized by fully developed speckle having a variance close to $(5.57 \text{ dB})^2$. For example, the comparator 52 of FIG. 9 can classify a variance as characteristic of soft tissue if it meets the relationship set out in Eq. 7:

$$\frac{|Var - (5.57)^2|}{(5.57)^2} < 0.5. \qquad \text{(Eq. 7)}$$

The actual local variance of speckle may not be equal to the theoretical value due to filters in the signal processing path of the ultrasound system. In practice the variance is determined through measurements on phantoms mimicking soft tissue.

Electronic noise itself has a variance close to that of soft tissue, and the AND operation indicated at 60 uses the SNR binary image and the variance binary image to avoid misclassification of electronic noise as soft tissue. This AND operation is performed on an element-by-element basis of the decimated SNR binary image and the decimated variance binary image. The resulting decimated tissue binary image has a value equal to zero if either the SNR binary image indicates that the associated region is characterized by low SNR ratio or the variance binary image indicates that the associated region is not soft tissue. The SNR binary image is not required in all embodiments, and other techniques can be used to avoid misclassifying regions of the image dominated by noise as soft tissue. For example, noise reduction techniques can be applied prior to local variance estimation.

The filtered, decimated image frame from the decimator 46 and the binary tissue image from the AND element 60 are applied as inputs to a device 62 for computing soft tissue intensity. In particular, the output of the device 62 is a decimated frame having intensity values that depend upon the corresponding values of the tissue binary image in the same region. Where the corresponding region of the tissue binary image is equal to logic value zero (indicating that the region does not correspond to soft tissue), the output of the device 62 does not include an intensity value for the corresponding region. Alternatively, for regions where the tissue binary image is equal to logic value one, the output of the device 62 includes the intensity value for the corresponding region as filtered by the filter 44 and decimated by the decimator 46.

In device 64 a surface, e.g., a second order surface, is fitted to the frame supplied by the device 62. This second order surface provides a measure of average soft tissue intensity as it varies throughout the image frame. Because of the use of the SNR binary image, portions of the image dominated by noise do not corrupt this second order surface. Because the surface is a second order surface fitted to a decimated frame, the surface fitted by device 64 does not vary so rapidly as to interfere with the presentation of transitions or interfaces between soft tissues of different contrasts.

Continuing with FIG. 9, the gain processor 34 of this embodiment uses a summer 82 to obtain the difference between the fitted surface from the device 64 and a soft tissue target intensity level $T_T$ on a region-by-region basis. The output of the summer 82 is a tissue gain $G_T$, which varies with both range and azimuth and is the gain required to cause the surface fitted to the local tissue mean to be displayed at the soft tissue target level $T_T$. This tissue gain $G_T$ is applied to a logic block 84 that also receives a second input $G_N$. The signal $G_N$ is generated by a summer 80 that takes the difference on a point-by-point basis between a noise target level $T_N$ and corresponding values of the filtered, decimated noise frame. Thus, the noise gain $G_N$ also varies with both range and azimuth, and represents the gain that is required to ensure that the local mean noise level is presented at the noise target level $T_N$. The logic block 84 sets the final two-dimensional gain equal $G_F$ to the lesser of $G_N$ and $G_T$. This final two-dimensional gain $G_F$ is applied to the image frame in block 86.

Figure 11:
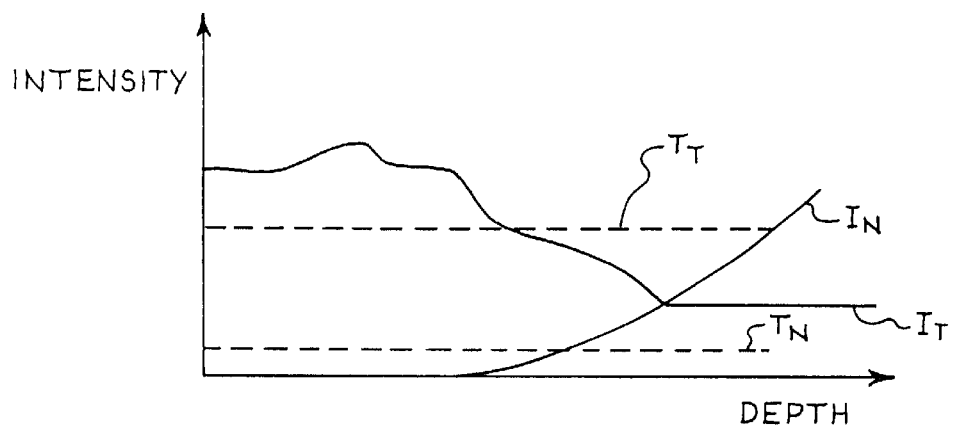
FIGS. 11, 12 and 13 are graphs illustrating operation of the embodiment of FIG. 9.
Figure 12:
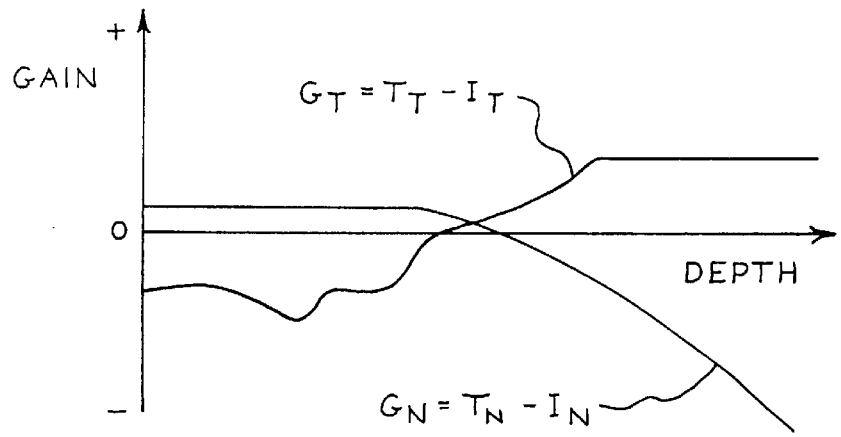
Figure 13:
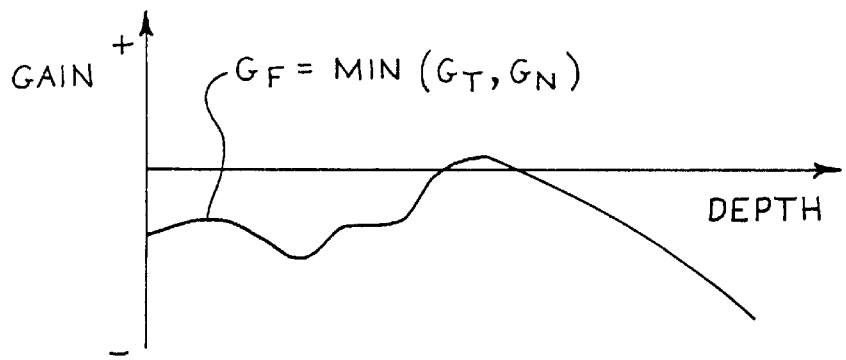

FIGS. 11–13 illustrate operation of the gain processor 34 of FIG. 9. In FIG. 11 the soft tissue target level $T_T$ and the noise target level $T_N$ are shown in dotted lines. In this case, $T_T$ and $T_N$ are both constant with depth. The noise intensity IN supplied by the decimator 42 and the tissue intensity $I_T$ supplied by the device 64 are shown in solid lines. In FIG. 12 $G_T$ and $G_N$ are illustrated, and in FIG. 13 the final gain $G_F$ is shown as the lesser of $G_T$ and $G_N$.

FIGS. 11–13 have been presented as two-dimensional graphs of intensity as a function of depth for clarity of illustration. As explained above, the gains $G_T$, $G_N$ and $G_F$ all vary in two dimensions as a function of both depth and azimuth.

The gain processor 34 sets the gain $G_F$ in such a way that the soft tissue regions of the image are displayed at about the tissue target level $T_T$ for all portions of the image where the noise signal is less than the noise target level. In regions of the image where the noise intensity $I_N$ is greater than a noise target level $T_N$ a lower gain is used to ensure that noise is not amplified inappropriately.

FIG. 10 provides a flowchart of a method implemented by the system of FIG. 9. In block 100 the adaptive gain features described above are initiated. This can be done in many ways. For example, adaptive gain can be initiated in response to user request or automatically at intervals. For example, adaptive gain can be automatically initiated every set number of frames or seconds.

Once adaptive gain has been initiated in block 100, control passes to block 102 where the image acquisition parameters of the system are set to preselected values. These preselected values optimize operation of the adaptive gain processor. By way of example the following general guidelines have been found suitable in one embodiment:

Image acquisition parameters, including gain and dynamic range, are determined so that, for the widest possible variety of imaging situations, the highest possible signal to noise ratio is maintained over the entire image without causing saturation of any portion of the image. This ensures that areas where the signal is weak are taken into account by the adaptive gain processor.

Once the image acquisition parameters have been selected, they are used to acquire one or more noise frames in block 104 and an image frame in block 106. As explained above, a noise frame is a conventional image frame, except that the transmitters are turned off. Since the transmitters are turned off there is no bona fide echo signal, and any signal appearing in the image frame is representative of system or electronic noise. The noise frame is used in block 108 to identify regions of image characterized by low SNR, as discussed above in conjunction with the creation of the SNR binary image. The image frame can be in any desired modality, and can for example include fundamental or harmonic imaging of tissue with or without added contrast agent.

Next, in block 110, a statistical measure of variability is determined for selected regions of the image frame. In block 110 the spatial or temporal mean of amplitude-detected, log-compressed signals can be used as described above. Alternately, the spatial variance of noise power normalized by the local mean of noise power can be used. For example, a normalized spatial variance can be determined on a pre-compression signal, where the normalized spatial variance is normalized by the local mean of the precompression signal.

The statistical measure of variability may be calculated along any one of the lateral, axial, and elevational axis, any two of these axes, or all three axes. The example described above calculates the variance over the lateral and axial axes.

Next, in blocks 112 and 114, regions of the image frame corresponding to soft tissue are determined. In block 114, the regions of the image characterized by low SNR as determined in block 108 are used to ensure that regions identified as soft tissue are outside of the noise-dominated regions of the image.

The local coherence factor may be used to ensure that regions of high acoustic noise or clutter are excluded from mapping decisions. The local coherence factor is defined as the ratio of the coherent (phase-sensitive) to the incoherent (phase-insensitive) summation across the receive channels of the delayed and apodized signals. See the discussion of Rigby U.S. Pat. No. 5,910,115. A low coherence factor indicates strong phase aberration, i.e., high levels of acoustic noise or clutter. Therefore using the coherence factor the regions of the image dominated by clutter can be ignored.

As explained above, this soft tissue identification can be done based on statistical measures of variability. Alternately, in some embodiments other methods may be used for identifying soft tissue, as for example methods based on the magnitude of the image signal. See the discussion of Klesenski U.S. Pat. No. 5,579,768, assigned to the assignee of the present invention.

At 116 a second order surface is fitted to the soft tissue intensity values over an entire frame, including both near-field and far-field portions of the frame.

At 118 the local gain is varied adaptively to cause signals having the amplitude of the second order surface at the respective locations to be displayed at a soft tissue target value over some or all of the image. The soft tissue target value or target display value can be set in many ways. The target display value may simply be a stored value or may be a user-selected value, or it may be a value adaptively determined in response to ambient light.

Alternatively and preferably, the soft tissue target level is a function of the currently invoked post-processing curve. Specifically a user controllable or predefined value may be used as a target soft-tissue gray level $T_G$. $T_T$ is then defined whenever a post-processing curve is selected to be the signal intensity level that is mapped to the display gray level of $T_G$.

Figure 14:
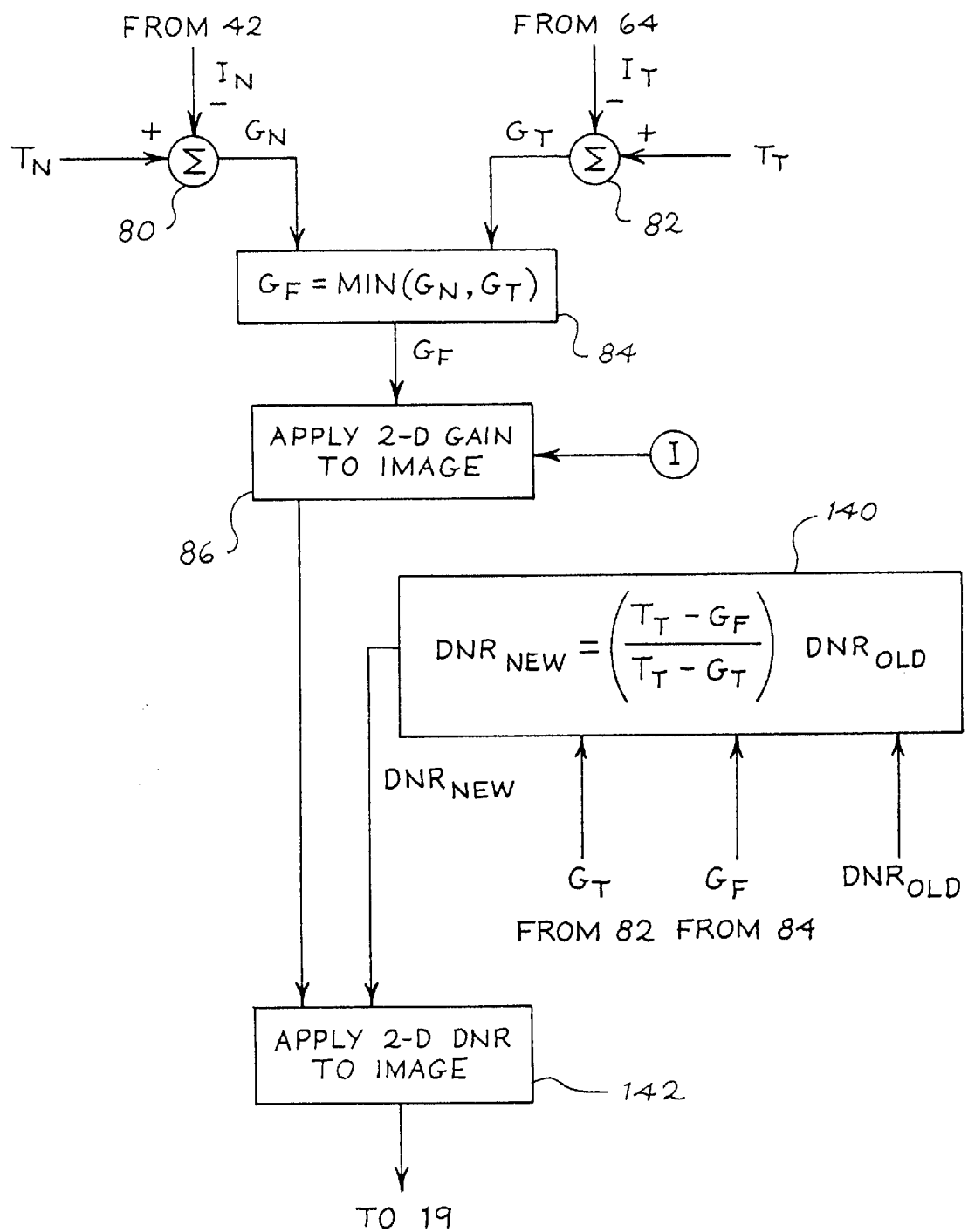
FIG. 14 is a block diagram of a second preferred embodiment of the gain processor of FIG. 8, which operates to set both local gain and local dynamic range adaptively.

FIG. 14 represents a second preferred embodiment of the gain processor of FIG. 8. The embodiment of FIG. 14 includes the summers 80, 82, the logic block 84 and the block 86, which may be identical to the corresponding elements of FIG. 9 discussed above. Additionally, the gain processor of FIG. 14 adaptively sets the dynamic range with which the image frame is displayed. In block 140 the final gain $G_F$, the tissue gain $G_T$ and a previously selected dynamic range $DNR_{OLD}$ are used to generate a new dynamic range $DNR_{NEW}$ according to the following equation:

$$DNR_{NEW} = \left(\frac{T_T - G_F}{T_T - G_T}\right) DNR_{OLD}. \tag{Eq. 8}$$

This new dynamic range $DNR_{NEW}$ is then applied to the gain-adjusted image generated by the block 86 to form a DNR-adjusted image to be applied to the display.

The gain processor of FIG. 14 adjusts the dynamic range in the low SNR region of the image. This adjustment of the dynamic range ensures that the soft tissue is on average displayed at the preselected target value $T_T$. Since the final gain $G_F$ and the tissue gain $G_T$ are functions of depth and azimuth, the new dynamic range $DNR_{NEW}$ is a spatially varying, adaptively determined quantity even when $DNR_{OLD}$ is not. The dynamic gain processor of FIG. 14 adaptively adjusts the SNR only in low SNR regions of the image, because in high SNR regions the final gain G is equal to the tissue gain $G_T$ and therefore in high SNR regions $DNR_{NEW}$ is equal to $DNR_{OLD}$.

The blocks 140, 142 of FIG. 14 adaptively vary the dynamic range of a signal based on both the soft tissue intensity and the noise level at a plurality of locations within the image.

Figure 15:
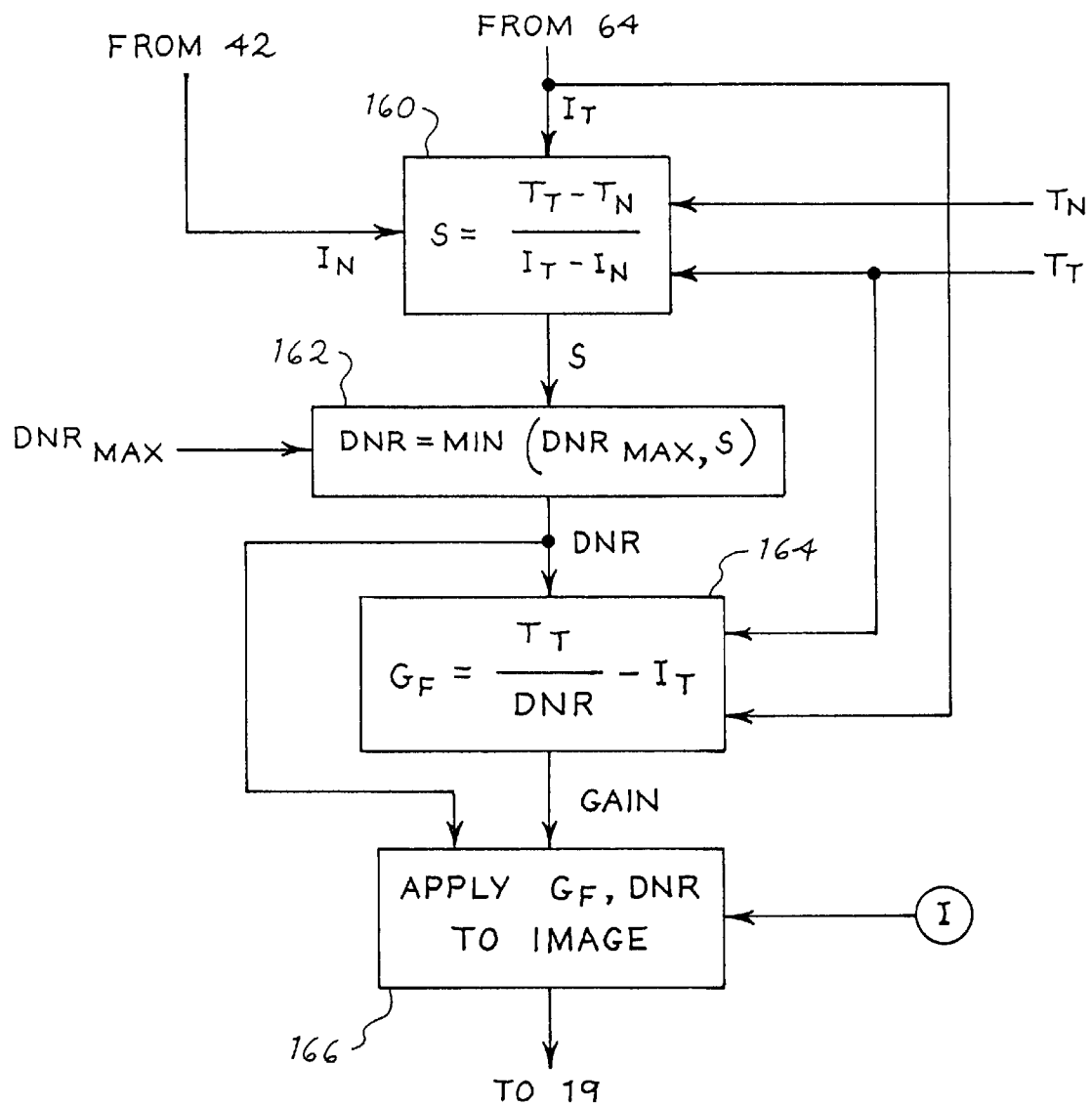
FIG. 15 is a block diagram of a third embodiment of the gain processor of FIG. 8, which operates to set both the local gain and the local dynamic range adaptively.

FIG. 15 shows a third preferred embodiment of the gain processor of FIG. 8. In the gain processor of FIG. 15, block 160 sets the parameter S according to the following equation:

$$S = \left(\frac{T_T - T_N}{I_T - I_N}\right), \tag{Eq. 9}$$

where $I_T$ is the local mean tissue intensity, $I_N$ is the local mean noise level, $T_T$ is the tissue target intensity and $T_N$ is the noise target intensity. In block 162 the dynamic range DNR is set equal to the minimum of the value S as determined by the block 160 and a maximum allowable dynamic range $DNR_{MAX}$. In block 164 a gain parameter is set according to Eq. 10:

$$G_F = \frac{T_T}{DNR} - I_T. \tag{Eq. 10}$$

Then, in block 166 the gain determined in block 164 and the dynamic range determined in block 162 are applied to the image frame.

Figure 16:
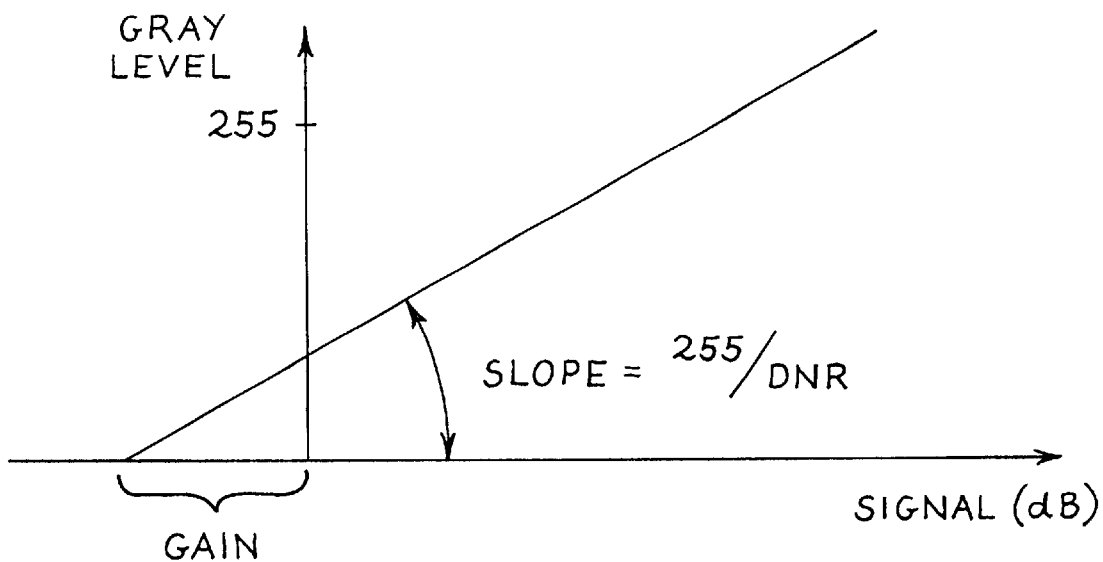
FIG. 16 is a graph used to explain operation of the embodiment of FIG. 15.

FIG. 16 will be used to explain the operation of the gain processor of FIG. 15. As shown in FIG. 16 the input signal is plotted on the horizontal axis in units of dB and the display gray level is plotted on the vertical axis. Here the slope of the line mapping the input signal to the display gray levels is inversely proportional to the dynamic range, in units of gray level per dB. Of course, the mapping function between the signal and the gray levels does not have to be linear, and in this case the slope of the line joining the gray levels that correspond to the minimum and maximum of the input signal of interest can be used. The gain in this example appears as shown, and the mapped gray level is equal to the slope multiplied by the sum of the signal plus the gain. With this relationship, the gain and dynamic range as determined by the embodiment of FIG. 15 map the average soft tissue intensity and the noise to the respective desired target values.

Of course, many alternatives are possible. In fact, the widest range of analog and digital signal processing techniques can be used to implement the basic functions described above. A programmed computer is one preferred implementation for the adaptive gain processor described above. For example, the adaptive gain and optionally the adaptively determined dynamic range can be applied to the image signals at any desired point along the signal path between the transducer array 13 and the display 19. Both can be applied before or after scan conversion, log compression and detection. The adaptive gain processor can operate on RF, IF or baseband signals before or after detection, log compression, and scan conversion.

Also, other methods can be used to determine the noise levels. For example, a computer model can be used that calculates noise level for various positions in the frame base on the parameters (including the acquisition parameters) of the imaging system.

The preferred embodiments described above combine a number of features that work together efficiently to adaptively set the gain and dynamic range of an image. It will be recognized that various ones of these features can be used separately from one another rather than in combination. In particular, the following inventions can be used together or in various subcombinations:

Using a statistical measure of variability to identify areas of an image corresponding substantially to soft tissue;

Fitting a surface to soft tissue intensity values, including soft tissue intensity values in both the near-field and the far-field portions of an image;

Acquiring an image for an adaptive gain system with a plurality of acquisition parameters of the system set to respective preselected values;

Adaptively varying a gain of an ultrasonic imaging system based at least in part on soft tissue intensity values and noise values at corresponding locations;

Adaptively varying dynamic range of an ultrasonic imaging system based at least in part on soft tissue intensity values and noise values at a plurality of locations in the image.

As used herein the term "image" is intended broadly to encompass images of one, two or three spatial dimensions. For example, an M-mode display can be considered a one-dimensional image.

The term "range of values" is intended broadly to encompass one or more values.

Two signals are said to be "comparable" whether they are equal in scale factor or differing in scale factor.

The term "soft tissue" is intended to refer to any target that produces speckle because of its unresolvable fine structure.

As indicated above, the maximum value of SNR may vary with time and any set of spatial coordinates.

The foregoing detailed description has been intended by way of illustration and not limitation. It is only the following claims, including all equivalents, that are intended to define the scope of this invention.

What is claimed is:

1. In a medical ultrasonic imaging system operative to acquire a receive input signal and to display an output signal, an adaptive mapping method comprising:
    (a) providing a noise signal indicative of a currently-prevailing noise level for the system; and
    (b) mapping the input signal to a noise range of output signal values when the input signal is comparable to the noise signal.

2. The method of claim 1 further comprising:
    (c) mapping the input signal to a soft tissue range of output signal values when the input signal is acquired from soft tissue.

3. The method of claim 1 further comprising:
    (c) mapping the input signal to a high-SNR range of output signal values when an SNR of the input signal relative to the noise signal is comparable to a maximum SNR of the input signal.

4. In a medical ultrasonic imaging system operative to acquire a receive input signal and to display an output signal, an adaptive mapping method comprising:
    (a) providing a noise signal indicative of a currently-prevailing noise level for the system;
    (b) mapping the input signal to a noise range of output signal values when the input signal is comparable to the noise signal; and
    (c) mapping the input signal to a high-SNR range of output signal values when an SNR of the input signal relative to the noise signal is comparable to a maximum SNR of the input signal.

5. In a medical ultrasonic imaging system operative to acquire a receive input signal and to display an output signal, an adaptive mapping method comprising:
    (a) providing a noise signal indicative of a currently-prevailing noise level for the system; and
    (b) mapping the input signal to a high-SNR range of output signal values when an SNR of the input signal relative to the noise signal is comparable to a maximum SNR of the input signal.

6. The method of claim 5 further comprising:
    (c) mapping the input signal to a noise range of output signal values when the input signal is comparable to the noise signal.

7. The method of claim 5 further comprising:
    (c) mapping the input signal to a soft tissue range of output signal values when the input signal is acquired from soft tissue.

8. In a medical ultrasonic imaging system operative to acquire a receive input signal and to display an output signal, an adaptive mapping method comprising:
    (a) determining a statistical measure of variability of the input signal;
    (b) identifying portions of the input signal corresponding to soft tissue based at least in part on the statistical measure of (a); and
    (c) mapping the portions of the input signal identified in (b) to a soft tissue range of output signal values.

9. The method of claim 8 further comprising:
    (d) providing a noise signal indicative of a currently-prevailing noise level for the system;
    (e) mapping the input signal to a noise range of output signal values when the input signal is comparable to the noise signal.

10. The method of claim 8 further comprising:
    (d) mapping the input signal to a high-SNR range of output signal values when an SNR of the input signal relative to the noise signal is comparable to a maximum SNR of the input signal.

11. The method of claim 9 further comprising:
    (f) mapping the input signal to a high-SNR range of output signal values when an SNR of the input signal relative to the noise signal is comparable to a maximum SNR of the input signal.

12. The method of claim 1, 4, 5, or 8 wherein the input signal is indicative of a multidimensional image.

13. The method of claim 3, 5, 10 or 11 wherein the SNR of the input signal is indicative of a point SNR.

14. The method of claim 13 wherein the maximum SNR is determined over a portion of the input signal corresponding to a portion of a current image frame.

15. The method of claim 14 wherein the maximum SNR is determined over a portion of the input signal corresponding to an entire current image frame.

16. The method of claim 14 wherein the maximum SNR is determined over a portion of the input signal corresponding to a previous image frame.

17. The method of claim 14 wherein the maximum SNR is determined over a portion of the input signal corresponding to N previous image frames, where N is an integer greater than 1.

18. The method of claim 3, 5, 10 or 11 wherein the SNR of the input signal is indicative of an average SNR.

19. The method of claim 18 wherein the maximum SNR is determined over a portion of the input signal corresponding to a portion of a current image frame.

20. The method of claim 18 wherein the maximum SNR is determined over a portion of the input signal corresponding to an entire current image frame.

21. The method of claim 18 wherein the maximum SNR is determined over a portion of the input signal corresponding to a previous image frame.

22. The method of claim 18 wherein the maximum SNR is determined over a portion of the input signal corresponding to N previous image frames, where N is an integer greater than 1.

23. The method of claim 1, 4, 5, 10 or 11 wherein the noise signal varies as a function of at least two spatial dimensions.

24. The method of clam 8 wherein (b) comprises:
(b1) determining high clutter portions of the output signal characterized by low coherence factor; and
(b2) ensuring that the areas identified in (b) are outside of the high clutter regions determined in (b1).

25. The method of claim 3, 4, 5, 10 or 11 wherein the maximum SNR of the input signal varies as a function of at least one spatial dimension.

26. The method of claim 3, 4, 5, 10 or 11 wherein the maximum SNR of the input signal varies as a function of at least two spatial dimensions.

27. The method of claim 1, 5 or 8 wherein the receive input signal is a signal selected from the group consisting of an intensity signal and an amplitude signal.

28. The method of claim 1, 5 or 8 wherein the receive input signal is a B-mode signal.

29. The method of claim 1, 5 or 8 wherein the receive input signal is a log-compressed signal.

30. In a medical ultrasonic imaging system operative to acquire an input signal indicative of an echo signal parameter and to display an output signal, an adaptive mapping method comprising:
(a) determining a statistical measure of amplitude variability of the input signal;
(b) identifying portions of the input signal corresponding substantially to soft tissue based at least in part on the statistical measure of (a);
(c) causing average amplitude of the portions of the input signal identified in (b) to be displayed at substantially a target display value.

31. The method of claim 30 wherein the statistical measure of (a) is indicative of spatial variance of the input signal, and wherein the input signal is amplitude-detected and log-compressed signals.

32. The method of claim 30 wherein the statistical measure of (a) is indicative of spatial variance of the input signal normalized by spatial local mean of the input signal, and wherein the input signal is a pre-compression signal.

33. The method of claim 30 wherein the statistical measure is determined in (a) along at least one axis selected from the group consisting of lateral, axial and elevational axes.

34. The method of claim 30 further comprising:
(d) storing the target display value as a pre-selected value.

35. The method of claim 30 further comprising:
(d) accepting user selection of the target display value.

36. The method of claim 30 further comprising:
(d) adaptively adjusting the target display value in response to ambient light.

37. The method of claim 30 wherein act (a) is automatically performed at a predetermined interval, and wherein the predetermined interval comprises a predetermined number of image frames.

38. The method of claim 30 wherein act (a) is automatically performed at a predetermined interval, and wherein the predetermined interval comprises a predetermined number of seconds.

39. The method of claim 30 wherein (b) comprises:
(b1) determining noise regions of the image characterized by low SNR; and
(b2) ensuring that the areas identified in (b) are outside of the noise regions determined in (b1).

40. The method of claim 30 wherein (b) comprises:
(b1) determining high clutter regions of the image characterized by low coherence factor; and
(b2) ensuring that the areas identified in (b) are outside of the high clutter regions determined in (b1).

41. In a medical ultrasonic imaging system, a method for adaptively controlling gain, said method comprising:
(a) determining soft tissue average amplitude in an ultrasound image at a plurality of locations of the image;
(b) fitting a surface to the soft tissue average amplitude in the image;
(c) adaptively varying a gain of the system based at least in part on the surface fitted in (b).

42. The method of claim 41 wherein the surface is a second order surface.

43. The method of claim 41 wherein (c) comprises:
(d) causing average amplitude of areas of soft tissue in the image to be displayed at substantially a target display value.

44. In a medical ultrasonic imaging system, a method for adaptively controlling gain, said method comprising:
(a) acquiring an ultrasound image with a plurality of acquisition parameters of the system set to respective pre-selected values;
(b) determining soft tissue average amplitude in the image at a plurality of locations of the image;
(c) adaptively varying a gain of the system based at least in part on the soft tissue average amplitude of (b).

45. In a medical ultrasonic imaging system, a method for adaptively controlling gain, said method comprising:
(a) determining soft tissue average amplitude in an ultrasound image at a plurality of locations in the image;
(b) determining noise values at said plurality of locations in the image; and
(c) adaptively varying a gain of the system based at least in part on the soft tissue average amplitude of (a) and the noise values of (b).

46. The method of claim 45 wherein (c) is operative to cause average amplitude of soft tissue to be displayed at substantially a target display value.

47. The method of claim 45 wherein (c) comprises subtracting the noise values from the image over at least a portion of the image.

48. The method of claim 45 wherein the noise values of (b) are indicative of spatial means of amplitude-detected, log-compressed noise at respective locations in the image.

49. The method of claim 45 wherein the noise values of (b) are indicative of temporal means of amplitude-detected, log-compressed noise at respective locations in the image.

50. The method of claim 45 wherein the noise values of (b) are indicative of spatial variance of noise power normalized by local mean noise power.

51. The method of claim 45 wherein the locations are arrayed in a one-dimensional array along a range axis of the image.

52. The method of claim 45 wherein the locations are arrayed in a two-dimensional array along range and azimuthal axes of the image.

53. In a medical ultrasonic imaging system, a method for adaptively controlling gain, said method comprising:
(a) determining soft tissue average amplitude in an ultrasound image at a plurality of locations in the image;
(b) determining noise values at said plurality of locations in the image; and (c) adaptively varying dynamic range of the system based at least in part on the average amplitude of (a) and the noise values of (b).

54. The method of claims 30, 41, 44, 45 or 53 further comprising:

(d) initiating (a), (b) and (c) in response to a user request.

55. The method of claims 30, 41, 44, 45 or 53 further comprising:

(d) initiating (a), (b) and (c) automatically at a predetermined interval.

56. The method of claim 53 further comprising:

(d) adaptively varying a gain of the system based at least in part on the average amplitude of (a) and the noise values of (b).

* * * * *